United States Patent

Ubasawa et al.

Patent Number: 5,604,209
Date of Patent: Feb. 18, 1997

[54] SYNERGISTIC ANTIVIRAL COMPOSITIONS

[75] Inventors: Masaru Ubasawa; Satoshi Yuasa, both of Yokohama, Japan

[73] Assignee: Mitsubishi Chemical Corporation, Tokyo, Japan

[21] Appl. No.: 253,274

[22] Filed: Jun. 2, 1994

[30] Foreign Application Priority Data

Jun. 3, 1993 [JP] Japan ................................ 5-133368

[51] Int. Cl.$^6$ ..................... A61K 31/505; A61K 31/52; A61K 31/70
[52] U.S. Cl. .............................. 514/45; 514/46; 514/47; 514/48; 514/49; 514/50; 514/51; 514/256; 514/269; 514/274; 514/885
[58] Field of Search ................................ 514/45, 46, 47, 514/49, 50, 269, 48, 51, 256, 274, 885

[56] References Cited

U.S. PATENT DOCUMENTS

| | | | |
|---|---|---|---|
| 4,724,232 | 2/1988 | Rideout et al. | 514/50 |
| 5,026,687 | 6/1991 | Yarchoan et al. | 514/45 |
| 5,071,983 | 12/1991 | Koszalka et al. | 514/49 |
| 5,318,972 | 6/1994 | Miyasaka et al. | 514/269 |

FOREIGN PATENT DOCUMENTS

| | | |
|---|---|---|
| 0420763 | 4/1991 | European Pat. Off. . |
| 0449726 | 10/1991 | European Pat. Off. . |

OTHER PUBLICATIONS

Molecular Pharmacology, vol. 39, No. 6, 1991, pp. 805–810, M. Baba, et al., "Highly Potent and Selective Inhibition of Human Immunodeficiency Virus Type 1 by a Novel Series of 6-Substituted Acyclouridine Derivatives".

Antimicrobial Agents and Chemotherapy, vol. 35, No. 7, Jul. 1991, pp. 1430–1433, M. Baba, et al., "Synergistic Inhibition of Human Immunodeficiency Virus Type 1 Replication by 5-Ethyl-1-Ethoxymethyl-6-(Phenylthio)Uracil (E–EPU) and Azidothymidine in Vitro".

Antimicrobial Agents and Chemotherapy, vol. 38, No. 4, Apr. 1994, pp. 688–692, M. Baba, et al., "Preclinical Evaluation of MKC-442, A Highly Potent and Specific Inhibitor of Human Immunodeficiency Virus Type 1 in Vitro".

Molecular Pharmacology, vol. 44, No. 4, Oct. 1993, pp. 895–900, S. Yuasa, et al., "Selective and Synergistic Inhibition of Human Immunodeficiency Virus Type 1 Reverse Transcriptase by a Non–Nucleoside Inhibitor, MKC–442".

Dialog Information Services, Inc., File 157:AIDSLINE, AN–00023673, S. Yuasa, et al., "Synergistic RT Inhibition of a New HEPT Derivative With AZT.TP," & International Conference on AIDS, Jun. 6–11, 1993, vol. 9, No. 1, p. 479.

*Primary Examiner*—James O. Wilson
*Attorney, Agent, or Firm*—Oblon, Spivak, McClelland, Maier & Neustadt, P.C.

[57] ABSTRACT

Antiviral agents which comprises as active ingredients one or more 2',3'-dideoxyribonucleosides or phosphoric esters thereof and 6-benzyl-1-ethoxymethyl-5-substituted uracil derivative of the formula (I):

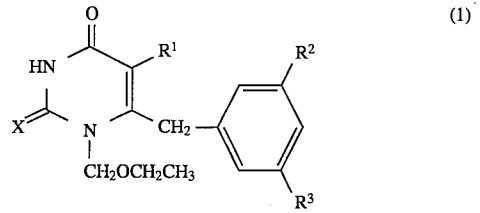

wherein X is oxygen or sulfur atom; $R^1$ is ethyl or isopropyl; $R^2$ and $R^3$ are independently hydrogen atom, $C_1$–$C_3$ alkyl or halogen atom, which compounds can inhibit HIV reverse transcriptase through different mechanisms and are synergistic in combination.

8 Claims, 1 Drawing Sheet

SYNERGISTIC ANTIVIRAL COMPOSITIONS

FIELD OF THE INVENTION

This invention relates to antiviral agents, more particularly, to pharmaceutical compositions which comprises as active ingredients two or more different kinds of antiviral substances capable of exerting synergistic effect in combination.

BACKGROUND OF THE INVENTION

Infections with human acquired immunodeficiency virus (HIV), a kind of retrovirus, have become one of gravest social problems in recent years. However, there are only three antiviral agents clinically available in the treatment of HIV infections at present. They all belong to nucleoside compounds, that is, 3'-azide-3'-deoxythymidine (AZT, Zidovudine), 2',3'-dideoxyinosine (ddI, Didanosine) and 2',3'-dideoxycytidine (ddC, Zalcitabine).

Although these existing nucleoside compounds can inhibit HIV reverse transcriptase, often through the inhibition of their triphosphorylation, and are potent antiviral agents, they have problems of various side effects and are highly toxic. For example, it has been reported that AZT may cause severe anemia or leukopenia due to suppression of bone marrow and ddI may cause peripheral nervus disorders or acute pancreatitis.

Further, a long-term treatment with these nucleoside derivatives can result in the appearance of drug-resistant mutant, which is a serious problem among practitioners.

Lately, there have been developed compounds that inhibit HIV reverse transcriptase through a novel mechanism, which are called "allosteric inhibitors" because they exert their effect by binding to "allosteric positions", i.e., those other than the substrate-binding-site, of the enzyme (European Patent Publication Nos. 384522, 429987, 462800, and 420763). These compounds are potent HIV inhibitors with less cytotoxicity compared to nucleoside compounds.

As the HIV infection is becoming more and more serious, it is strongly demanded to develop effective and low-toxic antiviral agents.

SUMMARY OF THE INVENTION

The present inventors have studied extensively with a purpose of providing antiviral agents which are useful in the treatment of HIV infections without serious side-effects. In the course of study, a combined use of two or more antiviral substances having distinct reaction mechanism interested the inventors as a possible approach to establish the purpose. Thus, they thought that if a combination composed of antiviral substances which are synergistic is provided, it must be greatly advantageous in various respects such as potent antiviral activity, low toxicity, reduction of dose and prevention of appearance of drug-resistant strains.

The present inventors have investigated into various combinations of a nucleoside compound, i.e., 2',3'-dideoxyribonucleoside, and many allosteric inhibitors, and have found that those containing as an allosteric inhibitor a 6-benzyl-1-ethoxymethyl-5-substituted uracil derivative can be extremely synergistic and useful for the establishment of the propose for the first time.

Thus, the present invention provides antiviral agents which comprises as active ingredients one or more 2',3'-dideoxyribonucleosides or phosphoric esters thereof and 6-benzyl-1-ethoxymethyl-5-substituted uracil derivative of the formula (I):

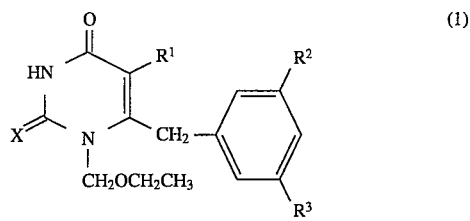

wherein X is oxygen or sulfur atom; and $R^1$ is ethyl or isopropyl; $R^2$ and $R^3$ are independently hydrogen atom, $C_1$–$C_3$ alkyl or halogen atom.

DETAILED DESCRIPTION OF THE INVENTION

Figure 1:
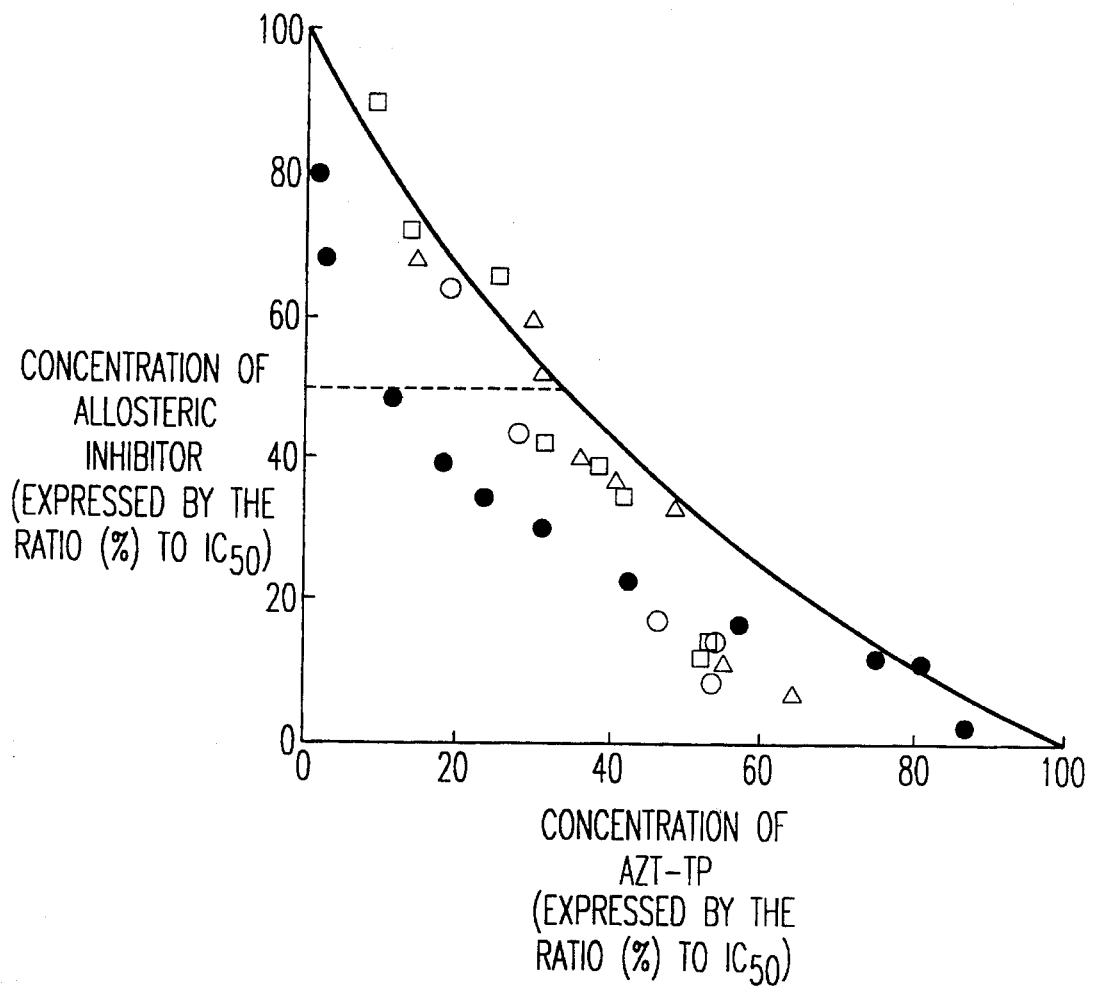

FIG. 1 depicts an isoborogram showing the inhibitory effect of combinations of 3'-azide-3'-deoxythymidine triphosphate (AZT-TP) and various allosteric inhibitors. The data plotted were obtained by dividing $IC_{50}$, the concentration of an allosteric inhibitor required to achieve 50% inhibition of reverse transcriptase of HIV, in the presence of a given concentration of AZT-TP with $IC_{50}$ of an allosteric inhibitor obtained in the absence of AZT-TP. In the FIG. 1, each symbol represents individual allosteric inhibitor as follows. Closed circle, 6-benzyl-1-ethoxymethyl -5-isopropyluracil (MKC-442); open square, (+)-(S)-9-chloro-4,5,6,7-tetrahydro-5-methyl-6-(3-methyl-2-butenyl)imidazo[4,5,1-jk][1,4]benzodiazepine-2(1H)-thione (R82913); open circle, 5,11-dihydro-11-cyclopropyl-4methyldipyrido[2,3,-b:2',3'-e][1,4]diazepine-6-one (Nevirapine); and open triangle, 3-[2-(benzoxazole-2-yl)ethyl]-5-ethyl-6-methylpyridine-2(1H)-one (L-696229), and the curve shows the additive effect. The FIGURE shows that a combination of MKC-442 and AZT-TP is especially synergistic.

The antiviral agents of the present invention contains as active ingredient 6-benzyl-1-ethoxymethyl-5-substituted uracil derivative of the formula (I) and one or more 2',3'-dideoxyribonucleosides. The 6-benzyl-1-ethoxymethyl-5-substituted uracil derivative (I) is known in a literature (European Patent Publication No. 420763) and can be prepared in accordance with a method described in the literature or in any manners similar to the same.

Examples of $C_1$–$C_3$ alkyl group in the definition of $R^2$ and $R^3$ include methyl, ethyl, propyl and isopropyl. Examples of halogen atom include fluorine, chlorine, bromine and the like. For purposes of the present invention, compounds (I) wherein X is oxygen, and $R^2$ and $R^3$ are hydrogen atoms are preferred and, especially, those wherein $R^1$ is isopropyl are more preferred.

Examples of 2',3'-dideoxyribonucleoside or its phosphoric ester include compounds of the formula (II) and (III) below:

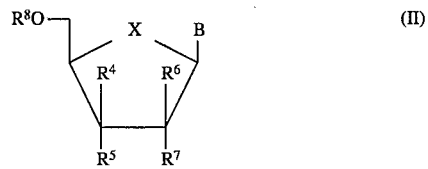

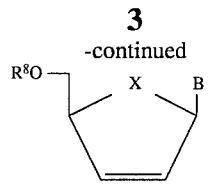

(III)

wherein B is pyrimidine residue or purine residue; X is oxygen atom or methylene; $R^4$–$R^7$ are independently hydrogen atom, azide, or halogen atom; and $R^8$ is hydrogen atom, —$PO(OH)_2$, —$PO(OH)OPO(OH)_2$ or —$PO(OH)OPO(OH)OPO(OH)_2$.

Examples of pyrimidine residue represented by B include cytosine, thymine, uracil, 5-fluorouracil, 5-fluorocitosine, 5-trifluoromethyluracil, 5-chlorouracil, 5-iodouracil. Examples of purine residue include adenine, guanine, hypoxanthine, xanthine, 2-fluoroadenine, 2,6-diaminopurine, 2-amino-6-chloropurine, 6-chloropurine and the like. For purposes of the invention, 2',3'-dideoxyribonucleoside compound is preferably 3'-azide-3'-deoxythymidine (AZT), 2,3'-dideoxyinosine (ddI) and 2',3'-dideoxycytidine (ddC), or phosphoric acid thereof. The most preferred one is AZT.

Preparation of 2',3'-dideoxyribonucleosides can be carried out using any one of known methods, for example, those described in J. Org. Chem., 29, 2076–2078 (1964); J. Org. Chem., 32, 817–818 (1967); J. Am. Chem. Soc. 86, 3585–3586 (1964); Yuki-gosei Kagaku (Organic Synthetic Chemistry), 48, 907–920 (1990); and Yuki-gosei Kagaku (Organic Synthetic Chemistry), 50, 535–544 (1992), or those analogous to the known methods. It is possible to purchase ddI and ddC and the like from P. L. Biochemicals, Inc.

The antiviral agents of the present invention can be used in treatment of infections with various kinds of viruses, especially retroviruses such as oncovirus, lentivirus, spumavirus and the like. Although the antiviral agents of the present invention are effective on viral infections caused by wide variety of virus, they are preferably used to treat or prevent lentivirus infection.

The antiviral agents of the present invention can be administered through various administration route, for example, oral, enteral, parenteral or topical route. The clinical dose of the antiviral agents varies depending on age, weight, conditions or the like of patient to be treated. Appropriate daily dosage of 6-benzyl-1-ethoxymethyl-5-substituted uracil derivative of the formula (I) to adult is generally about 1–100 mg/kg weight, preferably about 5–50 mg/kg weight and that of 2',3'-dideoxyribonucleoside or its phosphoric ester is generally about 1–100 mg/kg weight, preferably about 5–50 mg/kg weight, which may be administered once, or in two to several divisions at appropriate intervals.

The antiviral agents containing as active ingredients a 6-benzyl-1-ethoxymethyl-5-substituted uracil derivative and a 2',3'-dideoxyribonucleoside or phosphoric ester thereof can be administered in the form of separate or single formulation. In the former case, each ingredient is formulated into two independent formulations and administered simultaneously. In the latter case, both ingredients are formulated into a single formulation.

The ratio of 6-benzyl-1-ethoxymethyl-5-substituted uracil derivative and 2',3'-dideoxyribonucleoside or phosphoric ester in a single formulation can be preferably between 100:1 and 1:100, more preferably, 10:1 and 1:10. The dose of separate formulations will be determined on the basis of the ratios of active ingredients in a single formulation described above.

In such a case, one or more compounds selected from 2',3'-dideoxyribonucleosides or phosphoric esters can be used. For example, the following combinations are available.

(1) 6-Benzyl-1-ethoxymethyl-5-substituted uracil derivative+AZT;

(2) 6-Benzyl-1-ethoxymethyl-5-substituted uracil derivative+ddI;

(3) 6-Benzyl-1-ethoxymethyl-5-substituted uracil derivative+ddC;

(4) 6-Benzyl-1-ethoxymethyl-5-substituted uracil derivative+AZT+ddI;

(5) 6-Benzyl-1-ethoxymethyl-5-substituted uracil derivative+AZT+ddC;

(6) 6-Benzyl-1-ethoxymethyl-5-substituted uracil derivative+ddI+ddC; and (7) 6-Benzyl-1-ethoxymethyl-5-substituted uracil derivative+AZT+ddI+ddC.

In any case, it is preferred to use the antiviral agents of the invention after formulating into appropriate compositions in association with pharmaceutically acceptable carriers, excipients or the like. Carriers can be solid or liquid ones used in the art. Examples of solid carrier include lactose, kaolin, sucrose, crystalline cellulose, corn starch, talc, agar, pectin, stearic acid, magnesium stearate, lecithin, sodium chloride and the like. Examples of liquid carrier include glycerin, peanut oil, polyvinylpyrrolidone, olive oil, ethyl alcohol, benzyl alcohol, propylene glycol, physiological saline, water and the like.

The pharmaceutical composition may be in any forms. When solid carriers are used, it can be tablets, powders, granules, capsules, suppositories, troches or the like. When liquid carriers are used, it can be syrups, emulsions, soft gelatin capsules, creams, gels, pastes, sprays, injections or the like.

The antiviral agents of the present invention, which comprises as active ingredients 6-benzyl-1-ethoxymethyl-5-substituted uracil derivative, an allosteric inhibitor of reverse transcriptase, and 2',3'-dideoxyribonucleoside or phosphoric ester thereof, a competitive antagonist of the enzyme, which are synergistic in combination, are expected to be highly active and low toxic, and to contribute to the reduction of administration dose and the prevention of appearance of drug-resistant strains.

Following examples further illustrate and detail the invention disclosed, but should not be construed to limit the invention.

REFERENCE EXAMPLE 1

Preparation of
6-Benzyl-1-ethoxymethyl-5-isopropyluracil
(MKC-442)

To a suspension of 5-isopropyluracil (18 g) in dichloromethane (230 ml) was added bis-trimethylsilylacetamide (60.7 ml) and the mixture stirred for 1 hr at room temperature. To the solution were added tetra-n-butylammonium iodide (0.46 g) and chloromethylethyl ether (10.7 ml) at room temperature and the mixture stirred for 1.5 hr. The resultant mixture was washed and partitioned with cooled water (50 ml) (×2). The organic layer was concentrated under reduced pressure. The residue was crystallized at room temperature from n-heptane (100 ml) to yield 1-ethoxymethyl-5-isopropyluracil (22.2 g). M.p., 78.4° C.

An 1N lithium diisopropylamide solution (357 ml) in tetrahydrofuran was cooled to −10°—15° C. in a stream of nitrogen and a solution of 1-ethoxymethyl-5-isopropyluracil (22.2 g) in tetrahydrofuran (100 ml) was added dropwise thereto at an appropriate rate to keep the temperature of reaction mixture at −10°—15° C. Stirring was continued for another 1 hr at −10°—15° C. after the completion of addition. To the mixture was added dropwise benzaldehyde at an appropriate rate to keep the temperature of reaction mixture at −10—15° C. The mixture was stirred for 1 hr at the same range of temperature. The reaction was quenched by the addition of acetic acid (40.8 ml) and the reaction solution was warmed up to room temperature. The resultant mixture was washed and partitioned with semi-saturated saline (100 ml). The organic layer was combined with hexane (220 ml) and extracted with 1N sodium hydroxide solution (150 ml) (×2). The aqueous layer was neutralized with hydrochloric acid and extracted with toluene (200 ml). The extract was concentrated under reduced pressure to remove toluene and the residue dissolved in pyridine (100 ml). To the solution was added acetic anhydride (270 g) and the mixture allowed to stand for 16 hr at room temperature. After addition of cooled water (100 ml), the mixture allowed to stand for another 16 hr at room temperature. After the aqueous pyridine solution was concentrated under reduced pressure, some crystals precipitated, which were collected by filtration yield 6-(α-acetoxybenzyl)-1-ethoxymethyl-5-isopropyluracil (13.3 g). M.p., 158° C.

To a solution of 6-(α-acetoxybenzyl)-1-ethoxymethyl-5-isopropyluracil (13.3 g) in dioxane (53 ml) was added 5% Pd/C (0.66 g) and the mixture stirred for 4 hr at 50° C. under an atmosphere of hydrogen at ordinary pressure. After removal of Pd/C, the solvent was removed by distillation under reduced pressure. The residue was crystallized from ethanol (50 ml) in a refrigerator to yield 6-benzyl-1-ethoxymethyl-5-isopropyluracil (MKC-442) (10 g). M.p., 109°–110° C.

REFERENCE EXAMPLE 2

Preparation of 2′,3′-Dideoxyribonucleoside

According to the method described in J. O. Chem., 29, 2076–2078 (1964), 3′-azide-3′-deoxythymidine (AZT) and AZT triphosphate (AZT-TP) were synthesized.

REFERENCE EXAMPLE 3

Preparation of Other Allosteric Inhibitors

The following allosteric inhibitors were prepared according to a method described in literatures:

1. (+)-(S)-9-Chloro-4,5,6,7-tetrahydro-5-methyl-6-(3-methyl-2-butenyl)imidazo[4,5,1-jk][1,4]benzodiazepine-2(1H)-thione ("R82913"), European Patent Publication No. 384522;

2. 5,11-Dihydro-11-cyclopropyl-4-methyldipyrido[2,3,-b:2′,3′-e][1,4]diazepine-6-one ("Nevirapine"), European Patent Publication No. 429987; and 3. 3-[2-(Benzoxazole-2-yl)ethyl]-5-ethyl-6-methylpyridine-2(1H)-one (L-696229), European Patent Publication No. 462800.

The compounds R82913, Nevirapine and L-696229 are shown by the formula (IV), (V) and (VI), respectively.

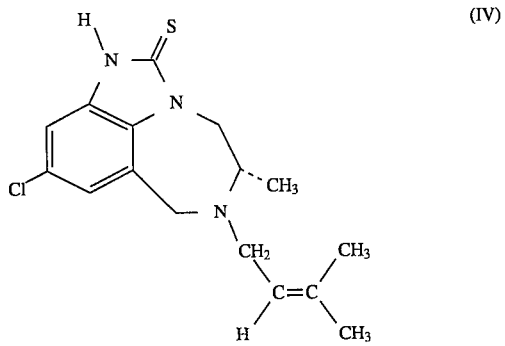

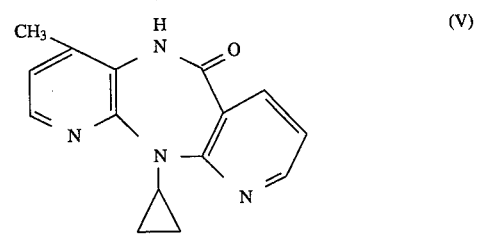

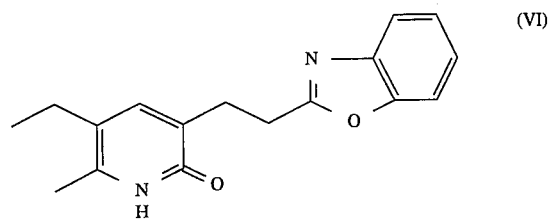

EXAMPLE 1

Evaluation of Inhibitory Activity of Antiviral Agent against HIV Reverse Transcriptase The inhibitory activity was evaluated on the basis of the incorporation of tritiated thymidine phosphate into acid-precipitating cDNA in the presence of HIV-1 reverse transcriptase (RT).

To a reaction solution (50 mM Tris-HCl, pH 8.4, 0.1% Triton X-100, 100 mM magnesium chloride, 2 mM dithiothreitol, 50 mM potassium chloride, 0.1 mg/ml bovine serum albumin (nuclease-free, Worthington, Freehold, N.J.), 0.5 μCi [methyl-$^3$H]TTP and 12 μg/ml poly(rA). p(dT)$_{12–18}$) was added 10% solution of a test drug in dimethyl sulfoxide and RT (0.05 units) to obtain a reaction mixture of total volume of 50 μl. The mixture was incubated at 37° C. for 30 min and the reaction stopped with 2M EDTA (10 μl). The resultant reaction mixture (50 μl) was spotted on Whatman DE-81 filter paper circle. The circle was washed with 5% disodium hydrogenphosphate (×3), water (×2) and 95% ethanol (×2) and the radiation was counted with scintillation counter. The activity of an allosteric inhibitor of HIV reverse transcriptase, which inhibits the incorporation of tritiated thymidine phosphate, was evaluated on the basis of the result obtained in the absence of test drug.

Thus, an isoborogram was prepared to evaluate the effect of combined use of AZT-TP and various allosteric inhibitors according to the method of Chou et al., Adv. Enzyme Regul., 22, 27–55 (1984) (FIG. 1). The data plotted were obtained by dividing IC$_{50}$, the concentration of an allosteric inhibitor required to achieve 50% inhibition of reverse transcriptase of HIV, in the presence of AZT-TP with IC$_{50}$ of an allosteric inhibitor obtained in the absence of a given concentration of AZT-TP. In the FIG. 1, each symbol represents individual allosteric inhibitor as follows. Closed circle, 6-benzyl-1-ethoxymethyl-5-isopropyluracil (MKC-442); open square, (+)-(S)-9-chloro-4,5,6,7-tetrahydro-5-methyl-6-(3-methyl-2-butenyl)imidazo[4,5,1-jk][1,4]benzodiazepine-2(1H)-thione (R82913); open circle, 5,11-dihydro-11-cyclopropyl-4methyldipyrido[2,3,-b:2',3'-e][1,4]diazepine-6-one (Nevirapine); and open triangle, 3-[2-(benzoxazole-2yl-)ethyl]-5-ethyl-6-methylpyridine-2(1H)-one (L-696229), and the curve shows the additive effect. The FIGURE shows that a combination of MKC-442 and AZT-TP is especially synergistic.

Thus, in the case of a combined use of MKC-442 and AZT-TP, the concentration of each compound required to obtain 50% inhibition of HIV-1 RT is unexpectedly lower than the IC50 of each compound. The $IC_{50}$ values of MKC-442 and AZT-TP, the concentration of a compound required to obtain 50% inhibition of RT when used alone, is 33.5 nM and 7.5 nM, respectively. As can be seen from the FIG. 1, the concentration of AZT-TP required to obtain 50% inhibition of RT is about 0.75 nM (about 1/10 of $IC_{50}$) in the presence of MKC-442 at an ½ concentration of $IC_{50}$. Such a remarkable synergistic effect was not observed in any other combinations of AZT-TP and allosteric inhibitors tested.

Combination indexes (CI) for 50%, 70% and 90% inhibition of RT (represented by $CI_{50}$, $CI_{70}$ and $CI_{90}$) were calculated according to the method of Prichard et al., Antimicrob. Agents Chemother., 35, 1060–1065 (1991) on the basis of results obtained in experiments carried out at least twice at indicated concentration ratio. Results are shown in Table 1 below, wherein CI<1 means the synergistic effect; CI1, additive effect; and CI>1, counterbalance effect. As can be seen from Table 1, the combination of MKC-442 and AZT-TP is synergistic at $CI_{50}$, $CI_{70}$ and $CI_{90}$ among various combinations of AZT-TP and an allosteric inhibitor.

TABLE 1

| Compound | AZT-TP/compound* | $CI_{50}$ | $CI_{70}$ | $CI_{90}$ |
|---|---|---|---|---|
| MKC-442 | 1/20 | 0.82 | 0.63 | 0.43 |
| R82913 | 1/250 | 1.15 | 1.33 | 1.70 |
| Nevirapine | 1/250 | 1.04 | 0.91 | 0.69 |
| L-696229 | 1/40 | 0.97 | 0.99 | 1.06 |

*The ratio of concentration of compounds in a combination, which was determined so that the $IC_{50}$ of individual compound in single use is almost the same.

EXAMPLE 2

Inhibition of HIV Infection

The inhibitory activity against HIV-1 infection was evaluated using MT-4 cells which are human T cell clones destined to die upon infection with HIV.

MT-4 cells were infected with HIV-1 (multiplicity of infection=0.02) in an RPMI1640 DM medium containing 20 mM Hepes buffer, 10% fetal bovine serum and 20 µg/ml gentamicin, which was followed by an immediate addition of a given amount of a composition prepared in dimethyl sulfoxide. The cells were incubated at 37° C. At 4th day of incubation, liable cells were counted by 3-(4,5-dimethylthiazole-2-yl)-2,5-diphenyltetrazolium bromide (MMT) method.

In a manner similar to that described in Example 1, combination indexes (CI) for 50%, 70% and 90% inhibition of death of MT-4 cells were calculated according to the method of Prichard et al., Antimicrob. Agents Chemother., 35, 1060–1065 (1991) on the basis of results obtained in experiments carried out at least three times at indicated concentration ratio. Results are shown in Table 2 below, wherein CI<1 means the synergistic effect; CI=1, additive effect; and CI>1, counterbalance effect. The results demonstrated that the combination of MKC-442 and AZT-TP is remarkably synergistic.

TABLE 2

| AZT-TP/MKC-442*[1] | Combination Index (CI)*[2] | | |
|---|---|---|---|
| | $CI_{50}$ | $CI_{70}$ | $CI_{90}$ |
| 1/8 | 0.60 | 0.40 | 0.21 |
| 2/8 | 0.53 | 0.36 | 0.20 |
| 4/8 | 0.60 | 0.39 | 0.21 |

*[1]The ratio of concentration in a combination.
*[2]Mean value of three experiments.

We claim:

1. A composition comprising an antiretroviral synergistic amount of 2',3'-dideoxyinosine and 6-benzyl-1-ethoxymethyl-5-isopropyluracil.

2. A composition comprising an antiretroviral synergistic amount of 3'-azide-3'-deoxythymidine and 6-benzyl-1-ethoxymethyl-5-isopropyluracil.

3. A composition comprising an antiretroviral synergistic amount of 3'-azide-3'-deoxythymidine triphosphate and 6-benzyl-1-ethoxymethyl-5-isopropyluracil.

4. A composition comprising an antiretroviral synergistic amount of 2',3'-dideoxycytidine and 6-benzyl-1-ethoxymethyl-5-isopropyluracil.

5. The composition as claimed in claim 1, wherein said composition is an anti-HIV composition.

6. The composition as claimed in claim 2, wherein said composition is an anti-HIV composition.

7. The composition as claimed in claim 3, wherein said composition is an anti-HIV composition.

8. The composition as claimed in claim 4, wherein said composition is an anti-HIV composition.

* * * * *